United States Patent [19]

Sarkar

[11] 4,397,954
[45] Aug. 9, 1983

[54] FLOWCELL FRACTIONATOR

[75] Inventor: Siddhartha Sarkar, Solana Beach, Calif.

[73] Assignee: The Regents of the University of California, Berkeley, Calif.

[21] Appl. No.: 323,100

[22] Filed: Nov. 19, 1981

Related U.S. Application Data

[62] Division of Ser. No. 155,227, Jun. 2, 1980, Pat. No. 4,326,026.

[51] Int. Cl.³ .................. A01N 1/02; C12M 1/00; B03D 1/00
[52] U.S. Cl. .................................. 435/287; 435/2; 209/158
[58] Field of Search .................. 435/2, 287, 284; 350/95; 209/11, 158, 159, 160, 161; 424/105

[56] References Cited

U.S. PATENT DOCUMENTS

| 2,942,520 | 6/1960 | Rose | 350/95 |
|---|---|---|---|
| 3,031,924 | 5/1962 | Lamal | 350/95 |
| 3,503,665 | 3/1970 | Carter | 350/95 |
| 3,829,216 | 8/1974 | Persidsky | 350/95 X |
| 3,976,197 | 8/1976 | Bhattacharya | 435/2 X |
| 4,007,087 | 2/1977 | Ericsson | 424/105 X |
| 4,009,260 | 2/1977 | Ericsson | 424/105 |
| 4,067,965 | 1/1978 | Bhattacharya | 424/105 |
| 4,225,405 | 9/1980 | Lawson | 435/2 X |

Primary Examiner—Robert J. Warden
Attorney, Agent, or Firm—Brown & Martin

[57] ABSTRACT

Enriched quantities of male and female sperm are obtained in physically separate fractions utilizing the hydrodynamic behavior of sperm in laminar flow. A flowcell fractionator is provided for performing the method, and includes a specially constructed pipette, valve and infusion pump combination.

10 Claims, 5 Drawing Figures

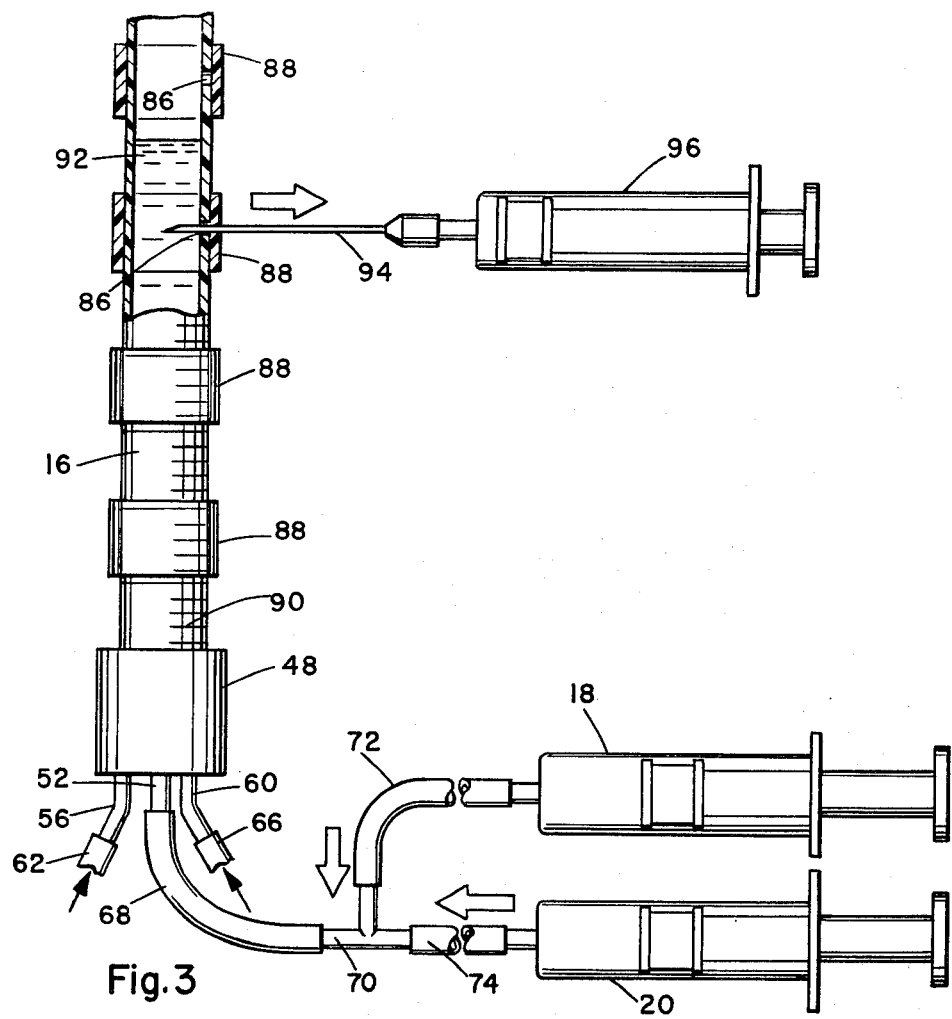
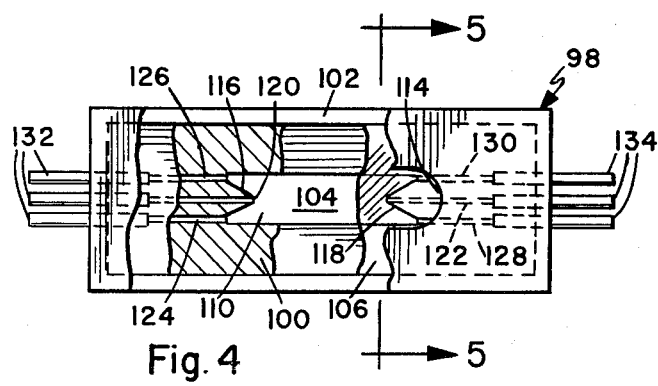
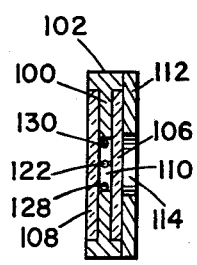

FLOWCELL FRACTIONATOR

CROSS-REFERENCE TO RELATED CASE

This is a division of U.S. patent appliction Ser. No. 155,227 filed June 2, 1980 and now U.S. Pat. No. 4,326,026 granted Apr. 20, 1982.

BACKGROUND OF THE INVENTION

The present invention relates to apparatus and methods for fractionating living cells according to specific physical characteristics. More particularly the present invention relates to a flowcell fractionator apparatus for obtaining from human semen enriched quantities of male and female sperm in physically separate fractions utilizing the hydrodynamic behavior of sperm in laminar flow.

Both the total number of sperm in an ejaculate and the percentage of sperm thereof which are motile, i.e. capable of progressive swimming movements, can be used as measures of the fertility of the sample, i.e. the liklihood that the sample will achieve fertilization. The motility of sperm has been observed since the earliest use of the microscope of Leeuwenhoek. The variety of techniques which have been developed to assess sperm motility have been summarized by R. W. Atherton in an article entitled "Evaluation of Sperm Motility" published in *Techniques of Human Andrology*, edited by E. S. E. Hafez, Chapter 7, pages 173–187, Elsevier/North-Holland Biomedical Press, 1977. On pages 181–182 of that article there is described a combination flowcell and spectrophotometer specially adapted for analyzing sperm motility based on orienting sperm in a flowing liquid, and then evaluating their return to randomness. While sperm motility analysis provides valuable information for determining fertility, it does not generally provide physically isolated enriched quantities of male and female fractions useable for artificial insemination.

U.S. Pat. No. 4,007,087 of Ericsson discloses a method of isolating a sperm fraction having a substantially enriched content of male (Y chromosome bearing) sperm. A special albumin solution is placed in a pipette and the albumin is overlaid with sperm. Male sperm swim to the bottom of the solution and the remainder can be culled off.

It would be desirable to provide a simpler, more effective way of obtaining enriched quantities of male and female sperm in physically separate fractions, and to ensure that the sperm in such fractions are motile and viable. It could be used to reduce the incidence of unsuccessful artificial inseminations of domestic animals, e.g. mares and cows. It could also be used to increase a man's natural fertility and to boost a couple's chances of having a boy.

SUMMARY OF THE INVENTION

It is an object of the present invention to provide an improved apparatus for obtaining enriched quantities of male and female sperm in physically separate fractions.

It is another object of the present invention to provide an apparatus for fractionating a wide variety of cells according to different physical characteristics thereof.

Still another object of the present invention is to provide an apparatus for separating male and female sperm by utilizing the hydrodynamic behavior of sperm under laminar flow conditions.

Yet another object of the present invention is to provide an apparatus which will enable the hydrodynamic behavior of sperm and other cells under laminar flow conditions to be observed and photographed under a microscope.

According to one embodiment of the present invention a prewarmed nutrient fluid is delivered by an infusion pump to a cap fit over the lower end of a vertical pipette. The nutrient fluid is introduced through three inlets in the cap. The three nutrient fluid inlets are directed to focus a cell suspension fluid injected through a central inlet in the cap. The cell suspension fluid is focused at a confluence region of the laminar flow generated by the incoming streams of nutrient fluid. The flow rate and pipette diameter are carefully chosen so that as the fluid level rises in the pipette a vertical gradient of different fractions of cells is established. When the pipette is nearly filled, fractions are collected at vertically spaced locations within the fluid column. This is done by inserting hypodermic needles through vertically spaced holes in the pipette. Sleeves made of an elastomeric material cover the holes in the pipette and are pierced by the hypodermic needles. In the case of human sperm, the various fluids are maintained at approximately 36° plus or minus 1° C. and the nutrient medium is specially adapted to maintain human sperm motility for long periods of time.

The present invention also provides a micro-flowcell fractionator apparatus for permitting the hydrodynamic behavior of sperm and other cells under laminar flow conditions to be observed and photographed through a microscope. This apparatus includes a rectangular frame having a central cutout region. Upper and lower glass slides overlie the frame and seal the cutout region to define a chamber. Triangular shaped projections forming part of the frame extend into the chamber at opposite ends thereof. A cell suspension fluid is introduced into the chamber at the apex of a first one of the triangular projections. Nutrient fluid is introduced through a pair of inlets on opposite sides of the cell suspension fluid inlet and adjacent the base of the triangular projection. The streams of fluid from the nutrient inlets thus create laminar flow within the chamber and focus the cells injected through the nutrient fluid inlet. The other end of the chamber has three corresponding and similarly positioned outlets. Micro-samples of fractionated material can be collected from the outlet which opens at the apex of the second triangular projection.

BRIEF DESCRIPTION OF THE DRAWINGS

FIG. 3 is an enlarged view of a portion of the apparatus of FIG. 1 illustrating the manner in which the cell suspension and nutrient fluids are injected into a single pipette and the manner in which a fluid sample containing a cell fraction is withdrawn.

FIG. 4 is a top plan view, with portions broken away, of a micro-flowcell fractionator apparatus constructed in accordance with a second embodiment of the present invention. It is utilized in a horizontal orientation for observing the hydrodynamic behavior of cells in lamanar flow under a microscope.

FIG. 5 is a sectional view of the micro-flowcell fractionator apparatus of FIG. 4 taking along line 5—5 of FIG. 4.

Throughout figures like reference numerals refer to like parts unless otherwise indicated.

DESCRIPTION OF THE PREFERRED EMBODIMENTS

Figures 1, 2:
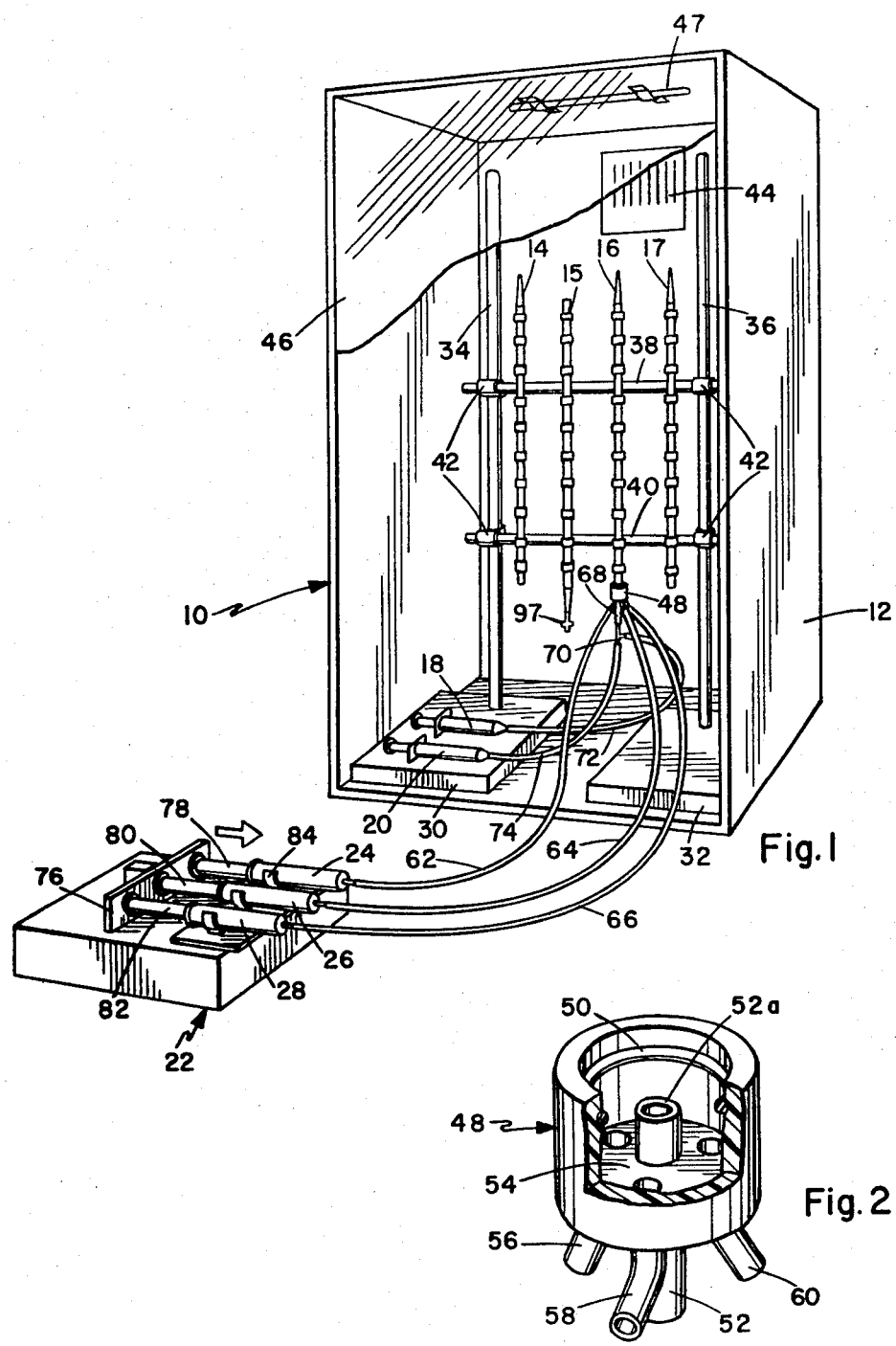
FIG. 1 is a perspective view of a complete flowcell fractionator apparatus constructed in accordance with a first embodiment of the present invention.
FIG. 2 is an enlarged perspective view, with portions broken away, of a pipette cap which forms a part of the apparatus of FIG. 1.

The two embodiments of the apparatus of the present invention which are described hereafter are particularly adapted for obtaining enriched quantities of male and female sperm is physically separate fractions and for permitting the observation of sperm hydrodynamic behavior in laminar flow. However, as more fully explained hereafter, the apparatus of the present invention can be utilized to fractionate cells other than human sperm according to a variety of criteria other than sex.

It is well known that motile sperm generally move upstream in a fluid against the direction of flow. This is because the flow generates a drag on the tail of the sperm which orients the head of the sperm so that it faces the direction of flow. Since motile sperm generally swim in a forward direction, sperm will move forward if their swimming velocity exceeds the flow rate. It is well known that motile sperm swim at different velocities. Generally female X sperm swim at slower velocities than male X sperm. I have discovered that enriched quantities of male and female sperm can be obtained in physically separate fractions from semen by utilizing the sperm hydrodynamic behavior in laminar flow. As used herein the term "laminar flow" refers to a streamlined, uniform flow in a fluid near a solid boundary without any significant turbulence.

Referring to FIG. 1, a first embodiment 10 of the flowcell fractionator apparatus includes an environmental chamber 12 which houses a plurality of vertically mounted elongate vessels or pipettes 14–17. In FIG. 1, the pipette 16 is connected for receiving nutrient and cell suspension fluids from a pair of manually operable syringes 18 and 20 and an infusion pump 22 including three electromechanically operated syringes 24, 26, and 28. A frame is provided within the environmental chamber for supporting the pipettes in precise vertical orientation. The frame includes a pair of heavy rectangular bases 30 and 32 having vertically extending rods 34 aand 36, respectively, secured thereto. A pair of horizontally extending rods 38 and 40 are ridgidly secured at their ends to the vertical rods 34 and 36 at vertically spaced locations by clamps 42. The pipettes 14–17 are secured to the upper and lower horizontal rods 38 and 40 by any suitable means such as adhesive but are preferably connected with clamps (not shown) so that the pipettes can be quickly replaced after use.

In order to obtain best results with regard to the fractionation of live cells, the cells must be suspended in a suitable nutrient fluid maintained at a temperature near that of their normal environment. Therefore, the apparatus of FIG. 1 includes a 600 watt electric heater with a fan (not shown) which delivers warm air through a louvered vent 44 in the rear wall of the environmental chamber 12. The front of the environmental chamber is preferably sealed, for example, with a removable layer of clear plastic 46. In the case of human sperm, the electric heater for the environmental chamber is thermostatically controlled to maintain the ambient air within the chamber at a temperature of approximately 36° plus or minus 1° C.

The temperature may be monitored by observing a thermometer 47 mounted to the ceiling of the environmental chamber. For best results, the fluid within the syringes 24, 26, and 28 should also be maintained at a temperature near that of the normal environment of the cells being fractionated. A second electric heater with a fan (not shown) may be positioned to blow warm air on the syringes of the infusion pump before and during the fractionation process.

The pipette 16 has a tapered open upper end, and an open lower end. A specially constructed cap 48 (FIGS. 1 and 2) is fit over the open lower end of the pipette 16 and sealed thereto by means of an O-ring 50. A cell suspension fluid inlet in the form of a tube 52 (FIG. 2) extends vertically and centrally through the cap 48. A cell suspension fluid is introduced in a vertical stream at the lower end of the chamber within the pipette at a location which coincides with the axis of the cylindrical chamber of the pipette. As shown in FIG. 2, the cell suspension fluid inlet 52 has a portion 52a extending above the bottom wall 54 of the cap.

Referring again to FIG. 2, a plurality of nutrient fluid inlets in the form of three angled tubes 56, 58 and 60 extend vertically through the bottom wall of the cap 48 at locations equally circumferentially spaced from each other and equally radially spaced from the cell suspension fluid inlet tube 52. The upper ends of the nutrient fluid inlets are flush with the bottom wall 54. The cell suspension and nutrient fluid inlets in the cap 48 are directed to establish a laminar flow longitudinally of the chamber within the vessel or pipette 16. A quantity of cell suspension fluid injected through the inlet 52 is focused at a central confluence region of the laminar flow generated by the incoming streams of nutrient fluid from the inlet 56, 58, and 60. By way of example, the inside diameter of the nutrient fluid and cell suspension fluid inlets may measure approximately 1.6 millimeters each.

Referring again to FIG. 1, hoses 62, 64, and 66 connect the nutrient fluid inlets 56, 58, and 60 (FIG. 2) with the syringes 24, 26, and 28 (FIG. 1) of the infusion pump 22, respectively. A short segment of hose 68 (FIG. 3) connects the cell suspension fluid inlet 52 with one leg of a three way T-shaped connector 70 (FIG. 1). Hoses 72 and 74 connect the other legs of the T-shaped connector with corresponding ones of the manually operable syringes 18 and 20, respectively.

In the apparatus of FIG. 1, pipettes have been utilized because they are readily available vessels which define small, elongate cylindrical chambers. Other vessels could be utilized. The essential flow parameters for optimal separation of human motile male and female sperm, and dead sperm, have been found experimentally to be dependent upon the flow rate and the diameter of the interior chamber of the vessel. A four hundred micron per second flow rate through a disposable plastic one milliliter pipette with a 0.2 centimeter internal diameter or a one hundred micron per second flow rate through a ten milliliter pipette with a 0.8 centimeter diameter have both given good separation results. The nutrient flow rate is preferably maintained nearly identical through each of the nutrient fluid inlets 56, 58, and 60 (FIG. 2). This is facilitated by the use of the infusion pump 22 (FIG. 1). This pump has an elongate rectangular plate 76 which is electromechanically moved in the direction indicated by the arrow in FIG. 1. The plate simultaneously depresses the pistons 78, 80, and 82 of each of the syringes mounted thereon. The syringes 24, 26, and 28 can each be separately filled prior to the fractionation process and inserted in removable clasps such as 84 on top of the pump. One suitable infusion pump is the Harvard model 975. The flow rate from each of the syringes 24, 26, and 28 can be adjusted as required between approximately 30 to approximately 500 microns per second.

Referring to FIG. 3, the pipette 16 has a plurality of vertically spaced holes 86 extending through its sidewall. A plurality of vertically spaced extraction valve means 88 are provided for permitting different vertically stacked fractions of the fluid within the pipette to be withdrawn through the holes 86. During the fractionation process the fluid within the pipette 16 rises. Due to the focusing of the cell suspension fluid at the central confluence region of the laminar flow imparted by the incoming nutrient streams, a longitudinal gradient of different fractions of the cells is established. The outer wall of the pipette 16 is provided with suitable level markers 90 for gaging the establishment of the gradient. Periodically samples of the fluid 92 within the pipette are withdrawn through a hypodermic needle 94 connected to a hypodermic syringe 96.

Each of the extraction valve means 88 may comprise a cylindrical sleeve made of an elastomeric material which surrounds the pipette 16 and overlaps one of the holes 86. A syringe needle such as 94 may be inserted through one of the sleeves and through one of the holes 86 to withdraw a fluid sample or fraction. Upon withdrawal of the hypodermic needle, a simple turning of the sleeve seals the hole and prevents any escape of fluid from the tiny laceration imparted by the hypodermic needle. The elastomeric sleeve thus acts in a similar manner to that of the human epidermis.

The manner in which the apparatus of FIG. 1 is utilized will now be described in greater detail. Whole human semen is preferably filtered through a 75 micron mesh filter made of a suitable material such as that sold under the trademark NITEX. Alternatively centrifuged and washed sperm may be utilized. Each of the syringes 24, 26, and 28 is loaded with an equal quantity of a special nutrient fluid which will maintain human sperm motility for long periods of time. One suitable nutrient fluid consists of RPMI (Roswell Park Memorial Institute) medium number 1640 available from GIBCO (Grand Island Biological Company) supplemented with 0.03 percent glutamine, penecillin (50 $\mu$g/ml), and 5 percent v/v preheated fetal calf serum. The nutrient fluid within the syringes of the infusion pump is preferably prewarmed with a hot air heater or other suitable heating means to maintain its temperature at approximately 36° plus or minus 1° C. The manually operable syringe 18 (FIGS. 1 and 3) is loaded with a predetermined amount of the same nutrient fluid. A predetermined amount of sperm suspended in a suitable fluid is loaded into the syringe 20 (FIGS. 1 and 3). The cell suspension fluid may consist of recently donated washed sperm mixed with a quantity of RPMI 1640. The interior of the environmental chamber is maintained at a temperature of approximately 36° plus or minus 1° C.

The infusion pump 22 is started and the warmed nutrient fluid which supports sperm viability is pumped into the interior chamber of the pipette 16 simultaneously through the three nutrient fluid inlets. As the fluid level rises in the pipette, a suitable amount of sperm suspension fluid from the syringe 20 is injected through the central inlet of the pipette cap at a steady pace. Preferably the amount of sperm suspension fluid which is injected is approximately one tenth of the volume of the pipette. For example, where the interior volume of the pipette is 10 milliliters approximately 1 milliliter of sperm suspension fluid is injected. Thereafter the remaining sperm cells in the hose 68 (FIG. 3) are flushed into the pipette at a steady pace with a predetermined amount of the nutrient fluid from the syringe 18. Preferably the amount of nutrient fluid used for flushing is also approximately one tenth of the pipette volume, i.e. approximately 1 milliliter where the pipette has an interior volume of 10 milliliters.

Undesirable effects can occur from uneven injection of the cell suspension and nutrient fluids via the manually operated syringes 18 and 20. To avoid this a single syringe can be utilized in connection with a second infusion pump (not shown) in place of the manually operated syringes 18 and 20. Initially this single syringe is loaded with the cell suspension fluid which is uniformly injected into the pipette by the second infusion pump. Thereafter the syringe in the second infusion pump is replaced with another syringe loaded with nutrient fluid. This nutrient fluid is uniformly injected into the pipette by the second infusion pump to flush the cells remaining in the hose 68.

As the fluid level within the pipette rises, the sperm suspension can be seen as a narrow central cylinder of fluid after it enters the pipette. The level of this cylinder rises slowly. The sperm is kept in focus at the center of the pipette as it meets the confluence region of the laminar flow generated by the incoming fluid streams from the three surrounding inlets 56, 58, and 60 (FIG. 2). The extended portion 52a of the cell suspension inlet 52 insures that the sperm is injected far enough upstream to be in the confluence region of the nutrient fluid streams.

The sperm cells are moved upward by the laminar flow, and are distributed evenly throughout the entire length of the fluid column. Large particles of debris, and defective but motile sperm cells, remain in the lower fractions. Dead cells and other debris tend to float at the moving boundary of the incoming fluid and are recovered in the upper most fractions. The rest of the sperm cells are distributed in the column of fluid both radially and longitudinally according to their hydrodynamic interaction with the radial and longitudinal cross-sectional velocities of the laminar flow. The quantities of fluid injected, and the pumping rate of the infusion pump 22 are maintained so that the fluid level rises slowly enough to establish a longitudinal or vertical gradient of different fractions of the cells. For example, when the fractionating vessel comprises a pipette having an interior volume of 10 milliliters, the fluid injection rates are controlled so that the pipette is filled over a period of approximately 30 minutes. During this time the interior of the environmental chamber is maintained at a temperature of approximately 36° plus or minus 1° C.

Fluid samples may be periodically withdrawn through the sleeves 88 and the holes 86 with the hypodermic needle and syringe 94 and 96 (see FIG. 3). The vertical point along the pipette at which the sample is withdrawn as well as the depth of penetration of the hypodermic needle within the interior chamber of the pipette will determine the character of the cell fraction withdrawn. A 100 $\mu$l volume sample can be withdrawn for microscopic observation during the process. The periodic withdrawal during the filling of the pipette is only for sampling purposes. At the end of the run, i.e.

when the pipette is nearly filled, the different fractions are collected with several syringes through the holes in the pipette. The collection is done starting at the top one of the sleeves 88 and the infusion pump is kept running during the sample collection to maintain the laminar flow. Sperm count in each fraction is obtained by utilizing a conventional COULTER counter. Motility is scored under a microscope, and an aliquot is centrifuged and processed to enumerate the proportion of male sperm in a given sample.

The apparatus of FIG. 1 and the method just described are designed to separate human sperm carrying the male sex determining chromosome from those carrying the chromosome which determines the female sex of the progeny. The male sperm can be recognized by a microscopic test which is used to determine the relative enrichment of the male sperm in a given sample. The absence of a characteristic male specific marker on the sperm suggests that it is probably a female sperm. Fractions enriched with either male or female sperm are obtained with this method and apparatus in a viable form and should be suitable for artificial insemination in humans. Tests performed with rabbits have verified the improved capabilities of the apparatus in altering the sex ratio of the progeny.

In the apparatus of FIG. 1, motile and viable sperm are automatically separated from debris and dead cells. At the same time male and female sperm are separated from one another. The motile sperm appears as a broadband. Male sperm are enriched near the leading edge of the flow, whereas female sperm are concentrated at the trailing edge. Motile sperm generally migrate slower than the leading edge of the flow. A two to four fold enrichment of male and female sperm has been obtained in extreme functions within the pipette. It is felt that sperm motility may not be essential for male and female sperm separation.

Sperm with genotypes other than or in addition to sex chromosome differences, may be separated utilizing the apparatus and method described above. The fractionation in laminar flow may be caused by the combined effect of many factors. Therefore, pathological features in sperm morphology, density, motility, and defects brought about by inherent or environmental factors may cause the defective sperm to separate from normal sperm. Normal sperm thus separated may be used for artificial insemination. Occurrences of birth defects may be prevented in this manner by separating sperm from carrying defective chromosomes, e.g. translocations, aneuploidy, etc., from normal sperm.

The apparatus of the present invention should be useful with other cell types which are not as obviously motile as sperm. Small cells having a diameter of six microns or less and which have different surface areas, density, size, and shape, could be separated with the present invention. Laminar flow either toward or against the force of gravity does not seem to significantly change the results of sperm fractionation, however, it may be an important consideration in separating certain cell classes.

The apparatus of the present invention may also prove to be useful for animal sperm selection in breeding or genetic studies. Minor changes in the design would probably be required to suit the differences in the sperm behavior of different species and the different semen volumes.

It should be understood that the method can be performed in several of the pipettes within the environmental chamber simultaneously by utilizing multiple pumps and syringes or by utilizing common pumps and syringes with appropriate connecting manifolds. This will enable larger volumes of enriched quantities of male and female sperm to be obtained in a given operating period.

Experiments have indicated that superior separation of X and Y sperm may be achieved by using a polystaltic pump in the place of the infusion pump 22. It delivers the nutrient fluid at a substantially constant rate, i.e., the fluid volume per unit time and the pulse period are constant. It is believed that the cyclical interruptions in fluid delivery which result when this pump is utilized is beneficial for separation.

Referring to FIG. 1, the pipette 15 may be utilized to perform a somewhat less sophisticated fractionation of cells such as sperm cells. This pipette has an open upper end and a three way coupling 97 connected to its open lower end. A first syringe (not shown) is utilized to inject a quantity of nutrient fluid into the pipette through one leg of the three way coupling to fill the pipette almost to the top. A second syringe (not shown) is used to inject a quantity of sperm suspension fluid into the pipette through a second leg of the three way coupling. Thereafter nutrient fluid is siphoned into the top of the pipette at a predetermined rate and fluid is drained from the third leg of the three way coupling to establish a laminar flow within the pipette. The flow rate is controlled to establish a vertical gradient of cell fractions within the pipette. These fractions are removed through vertically spaced holes in the pipette and through elastomeric sleeves which cover the same. A hypodermic needle is used to withdraw the functions as previously described. Thus as used herein the term "pump" includes not only electromechanical driven pumps but also pumps without any moving parts such as a reservoir raised to a height sufficient to generate a pressure head through a siphon.

FIGS. 4 and 5 illustrate a second embodiment of the flowcell fractionator apparatus of the present invention. It can be utilized under a microscope fitted with photographic equipment to make accurate measurement of flow parameters, movement and sperm of other cell orientation under laminar flow conditions and to obtain fractionated micro-samples. The information from the utilization of this micro-flowcell fractionator can be utilized to optimize the operating parameters of the apparatus disclosed in FIG. 1.

The micro-flowcell fractionator 98 illustrated in FIGS. 4 and 5 includes a rectangular frame 100 having a surrounding outer flange 102 and a central cut out region 104. A pair of upper and lower rectangular glass slides 106 and 108 overlie the frame on opposite sides thereof and seal the cut out region to define a chamber 110. The glass slides are held in alignment by the surrounding flange 102 of the frame. The glass slides may be sealed to the frame about their perimeter with stopcock grease available from Dow Chemical Corporation and others. A rectangular metal cover plate 112 having the same outer dimension as the frame 100 rests on the flange 102 and covers the upper glass slide 106. The metal plate has a centrally located oval aperture 114 which is slightly larger than the cut out region 104 and enables the fluid within the chamber 110 to be observed through the microscope. The top cover plate may be secured to the frame by screws, glue or other suitable means. The lower glass slide 108 may also be secured to the frame by glue or other suitable attachment means.

The frame 100 of the micro-flowcell fractionator includes a pair of triangular projections 116 and 118 (FIG. 4) which project into the chamber 110 at opposite ends thereof. A cell suspension fluid inlet 120 extends through one end of the frame and opens into one end of the chamber at the apex of the triangular projection 116. Likewise a cell suspension fluid outlet 122 extends through the other end of the frame and opens into the other end of the chamber at the apex of the other triangular projection 118. A pair of nutrient fluid inlets 124 and 126 extend through the frame and open into the chamber at one end thereof on opposite sides of the cell suspension fluid inlet 120. These inlets are located adjacent the base of the triangular projection 116. Similarly a pair of nutrient fluid outlets 128 and 130 extend through the other end of the frame and open into the other end of the chamber. These outlets are located on opposite sides of the cell suspension fluid outlet 122 adjacent the base of the second triangular projection 118. Three inlet tubes 132 are connected to the inlets 120, 124 and 126. Three outlet tubes 134 are connected to the outlets 122, 128 and 130.

The relative sizes of the various inlets and outlets of the microflowcell fractionator as well as the size of the chamber 110 depend upon the type of cells which are to be introduced into the fractionator and observed. In the case of human sperm, the inlets and outlets which open into the chamber may have an inside diameter of approximately 0.8 millimeters and the distance between adjacent ones of these inlets and outlets may be approximately 3.5 millimeters. The depth, width, and length of the chamber 110 may be approximately 1.15 millimeters, 8 millimeters, and 33 millimeters, respectively.

The micro-flowcell fractionator of FIGS. 4 and 5 may be used in the following manner. The apparatus is mounted under the lense of a suitable microscope having photographic equipment optically coupled thereto. Nutrient fluid delivered at a constant predetermined rate from an infusion pump (not shown) is delivered through hoses (not shown) connected to the two outer ones of the inlet tubes 132. The cell suspension fluid is injected through the center one of the inlet tubes 132 and through the inlet 120. The cells in this fluid are focused by the two incoming lateral streams of nutrient fluid from the inlets 124 and 126. This focusing occurs at a central confluence region of the laminar flow generated by the incoming nutrient fluid. The central confluence region is visible through the aperture 114. Accurate measurements of the flow rate at the radial and longitudinal cross sections of the flow path can be made, along with accurate measurements of the orientation and behavior of live and dead sperm in the laminar flow. The behavior of other cells in the hydrodynamic field within the chamber 110 can be observed before attempting fractionation in the apparatus of FIG. 1. Micro-samples of the fractionated material can be collected at the central one of the outlet tubes 134 at short time intervals to assess the efficiency of separation. Cell behavior in laminar flow can be observed directly through the microscope or can be photographed by the photographic equipment optically coupled to the microscope.

The micro-flowcell fractionator apparatus illustrated in FIGS. 4 and 5 can be used to determine cell behavior in complicated flow conditions because direct observations can be made under a microscope. The triangular projections and the staggering of the various inlets permit the most efficient focusing of the cells in the laminar flow and the most efficient extraction of cells from the other end of the device. The micro-flowcell fractionator can also be utilized in contraceptive research because the pharmacological effects of drugs on sperm behavior can be directly visualized and quantified on a time dependent basis.

Isolation of X chromosome bearing sperm may be achieved by combining mechanical and biochemical selective techniques. For example, in connection with the utilization of the apparatus of FIG. 1, sperm motility can be made conditionally dependent upon the utilization of hypoxanthine by the X-linked enzyme activity, EC 2.4.2.8. hypoxanthine phosphoribosyl transferase (HPRT), when the de novo pathway of purine synthesis is inhibited with aminopterin. Under this selection condition, the Y chromosome positive sperm loose their motility faster than the Y chromosome negative cells, thereby allowing one to enrich for X chromosome bearing sperm in the motile fraction obtained with the apparatus of FIG. 1. Immunofluorescense staining of sperm HPRT shows that the enzyme has a broad quantitive variation among sperm populations unlike the all or none distribution of sex chromosomes.

Having described preferred embodiments of my apparatus, it should be apparent that my invention permits of modification in both arrangement and detail. Therefore the protection afforded my invention should be limited only in accordance with the scope of the following claims.

I claim:
1. An apparatus for fractionating cells comprising:
  a vessel defining an elongate chamber;
  a cell suspension fluid inlet centrally positioned at one end of the chamber;
  a plurality of nutrient fluid inlets positioned at the one end of the chamber surrounding the cell suspension fluid inlet;
  means for pumping a nutrient fluid through the nutrient fluid inlets at a substantially constant rate; and
  means for injecting a predetermined quantity of a cell suspension fluid through the cell suspension fluid inlet;
  the cell suspension and nutrient fluid inlets being directed to establish a laminar flow longitudinally of the chamber as the nutrient fluid is pumped therethrough and so that the quantity of cell suspension fluid injected through the cell suspension fluid inlet is focussed at a central confluence region of the laminar flow.

2. An apparatus according to claim 1 wherein
  the vessel is a vertically extending pipette having a plurality of vertically spaced holes extending through a sidewall thereof;
  the inlets are positioned at the lower end of the pipette; and
  the pipette has a plurality of vertically spaced surrounding elastomeric sleeves each overlapping one of the holes in the pipette for permitting different fractions of the fluid within the pipette to be withdrawn through the holes with a hypodermic needle.

3. An apparatus of claim 1 wherein the pump means includes an infusion pump.

4. An apparatus of claim 1 wherein a cap is sealed over the lower end of the vessel, the cell suspension fluid inlet extends centrally and vertically through the cap and the nutrient fluid inlets extend vertically through the cap at locations equally circumferentially spaced from each other and equally radially spaced from the cell suspension fluid inlet.

5. An apparatus according to claim 1 and further comprising environmental chamber means housing the vessel for maintaining fluid within the vessel at a temperature of from approximately 35° C. to approximately 37° C.

6. An apparatus according to claim 1 wherein the injecting means includes:
   a three way connector having three legs;
   a cell suspension fluid syringe connected to a first leg of the connector;
   a nutrient fluid flush syringe connected to a second leg of the connector; and
   a tube connecting the third leg of the connector with the cell suspension fluid inlet.

7. An apparatus according to claim 1 wherein the vessel includes:
   a rectangular frame having a central cut out region;
   a pair of glass slides overlying the frame on opposite sides thereof and sealing the cut out region to define the chamber;
   the suspension fluid inlet extends through one end of the frame and opens into one end of the chamber; and
   a pair of nutrient fluid inlets extend through the one end of the frame and open into the chamber on opposite sides of the cell suspension fluid inlet.

8. An apparatus according to claim 7 wherein the cell suspension fluid inlet opens into the chamber at the apex of a first triangular projection of the frame at the one end of the chamber and the nutrient fluid inlets open into the chamber adjacent the base of the triangular projection.

9. An apparatus according to claim 8 wherein the frame includes:
   a second triangular projection at the other end of the chamber;
   a cell suspension fluid outlet extending through the other end of the frame and opening into the chamber at the apex of the second triangular projection; and
   a pair of nutrient fluid outlets extending through the other end of the frame and opening into the chamber adjacent the base of the second triangular projection.

10. An apparatus for fractionating sperm comprising:
    a vertically extending chamber;
    means for injecting a sperm suspension fluid into the chamber;
    means for establishing a vertical laminar flow of a nutrient fluid within the chamber to establish a vertical gradient of different fractions of the sperm; and
    a plurality of vertically spaced extraction valve means for permitting fluid samples containing individual ones of the sperm fractions to be withdrawn from the chamber.

* * * * *